United States Patent
Henderson et al.

(10) Patent No.: US 10,940,130 B2
(45) Date of Patent: Mar. 9, 2021

(54) COMPOSITIONS COMPRISING THEANINE AND WHEY PROTEIN

(71) Applicant: NUTRAMAX LABORATORIES, INC., Lancaster, SC (US)

(72) Inventors: Todd Henderson, Lancaster, SC (US); David Griffin, Forest Hill, MD (US); David Bledsoe, Lancaster, SC (US)

(73) Assignee: NUTRAMAX LABORATORIES, INC., Lancaster, SC (US)

( * ) Notice: Subject to any disclaimer, the term of this patent is extended or adjusted under 35 U.S.C. 154(b) by 0 days.

(21) Appl. No.: 16/437,701

(22) Filed: Jun. 11, 2019

(65) Prior Publication Data

US 2019/0290608 A1 Sep. 26, 2019

Related U.S. Application Data (63) Continuation of application No. 15/705,435, filed on Sep. 15, 2017, now Pat. No. 10,335,384, which is a continuation of application No. PCT/US2016/049630, filed on Aug. 31, 2016.

(60) Provisional application No. 62/212,080, filed on Aug. 31, 2015.

(51) Int. Cl.
| | |
|---|---|
| *A61K 31/198* | (2006.01) |
| *A61K 36/756* | (2006.01) |
| *A61K 38/01* | (2006.01) |
| *A61K 45/06* | (2006.01) |
| *A61K 31/7076* | (2006.01) |
| *A61K 9/00* | (2006.01) |
| *A61K 31/197* | (2006.01) |
| *A61K 31/4045* | (2006.01) |
| *A61K 36/575* | (2006.01) |
| *A61K 38/38* | (2006.01) |

(52) U.S. Cl.
CPC ......... *A61K 31/198* (2013.01); *A61K 9/0053* (2013.01); *A61K 31/197* (2013.01); *A61K 31/4045* (2013.01); *A61K 31/7076* (2013.01); *A61K 36/575* (2013.01); *A61K 36/756* (2013.01); *A61K 38/018* (2013.01); *A61K 38/38* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2013/0156872 | A1* | 6/2013 | Giuliano | A61K 36/48 424/757 |
| 2015/0125548 | A1* | 5/2015 | Knutsen | A23L 33/10 424/641 |
| 2015/0272989 | A1* | 10/2015 | Roberts | A61K 33/08 424/693 |
| 2016/0271198 | A1* | 9/2016 | Jones | A23L 33/175 |
| 2018/0169163 | A1* | 6/2018 | Geng | A61K 36/185 |

FOREIGN PATENT DOCUMENTS

| | | |
|---|---|---|
| JP | 2009500319 A | 1/2009 |
| JP | 2012206942 A | 10/2012 |
| WO | 2007004244 A1 | 1/2007 |

OTHER PUBLICATIONS

JP 2009500319A—English machine translation.
JP 2012206942A—English machine translation.

* cited by examiner

*Primary Examiner* — Ralph J Gitomer
(74) *Attorney, Agent, or Firm* — King & Schickli, PLLC (57) ABSTRACT

An anxiolytic composition includes a synergistic combination of an L-theanine and a whey protein composition.

10 Claims, 6 Drawing Sheets

COMPOSITIONS COMPRISING THEANINE AND WHEY PROTEIN

This application is a continuation of U.S. continuation patent application Ser. No. 15/705,435 filed on Sep. 15, 2017, which is a continuation patent application claiming priority to International Application No. PCT/US2016/049630 filed on Aug. 31, 2016, which in turn claims priority to U.S. Provisional Patent Application Ser. No. 62/212,080 filed on Aug. 31, 2015, the entirety of the contents of each of which are incorporated by reference herein.

TECHNICAL FIELD

The present application relates generally to anxiolytic compositions containing *magnolia*, phellodendron, theanine, a whey protein, and/or s-adenosylmethionine.

BACKGROUND

Anxiety, fear, and stress play major roles or contribute in some way to many human and non-human animal behavioral disorders. For example, with regard to canines and felines, storm phobias, noise phobias, social avoidance, fear-related aggression, compulsive disorders, and submissive urination have obvious anxiety components, but even problems such as urine marking, territorial aggression, and resource guarding can be fueled by fear or anxiety. Fear and anxiety disorders affect an estimated 23 million dogs in the US at a cost of more than $1 billion in treatment and property damage. Of dogs relinquished to shelters, perhaps 40% or more are abandoned due to behavioral issues, while 14% of cats are surrendered due to behavioral problems. In pet cats, behavior problems are still the most common cause of euthanasia. In a recent survey of pet owners, 41% of dog owners reported that they have owned a dog with anxiety issues at some time, with 29% of currently-owned dogs being affected. The most prevalent types of anxiety reported by these owners included noise phobia (17%), separation anxiety (13%), and generalized anxiety (5%).

Anxiety in horses is similarly a common problem in the equine industry, contributing to behavioral problems, training issues and poor performance. In some cases, increased levels of anxiety are associated with health related issues such as gastric ulcers, which have been shown in some studies to impact a large percentage of horses. Manifestations of anxiety in horses is commonly seen not only in the form of gastric ulcers, but also is expressed behaviorally in the form of bolting, jumping, panicking, trailering difficulties, pacing, stall weaving, pawing, and biting. The most common risk factor for anxiety disorders in dogs appears to be acquisition from animal shelters or multiple foster homes, with up to 68.3% of dogs adopted from shelters exhibiting some type of anxiety disorder. One retrospective study on behavior diagnoses indicates possible breed predilections in Dalmatians, English springer spaniels, German shepherd dogs, and mixed breed dogs, while another study suggests cocker spaniels, schnauzers, and dachshunds may be at risk for developing separation anxiety. The incidence of anxiety disorders does appear to increase with age, most likely due to a loss of cognitive function, from an incidence of 22.5% in dogs less than 3 years of age to an incidence of 36.5% in dogs 8 years of age and over.

Fear is an emotional response due to the presence of a specific stimulus (object, noise, individual, etc.) that the pet perceives as a threat or a danger. In contrast, an anxiety is a reaction of apprehension or uneasiness to an anticipated danger or threat. Anxiety, therefore, may be displayed in the absence of an identifiable stimulus, whereas with fear, a stimulus can usually be identified. While anxiety and the accompanying physiological stress are unlikely to be pathologic in the short-term, when stress and anxiety become a chronic state, the health, welfare, and lifespan of the pet may become compromised. Therefore, to provide optimum health and welfare for all pets, veterinary healthcare practitioners consider anxiety as an additional possible disease state in companion animals. At the extreme end of the spectrum, a phobia is a profound, excessive, abnormal fear response that occurs without the presence of a true threat or is out of proportion to the needs for dealing with an actual threat. While fears may be normal adaptive responses, phobias are abnormal, maladaptive, and typically interfere with normal function. Anxiety, which inhabits the middle of the spectrum, is often overlooked or misunderstood, but may have a significant impact on a pet's daily well-being.

Clinical signs of fear and anxiety in dogs include hyper-vigilance, elimination, destruction, excessive vocalization, hyper-salivation, panting, hiding, trembling, and escape behaviors. In cats, chronic anxiety and fear can also lead to secondary behavioral problems such as over-grooming, spraying, and inter-cat aggression, and can predispose the cat to health problems owing to a compromised immune system. Since most of the clinical signs of fear and anxiety are destructive and distressing to both pet and owner, one can easily understand why pet owners would be likely to seek out advice for such disorders. Not coincidentally, the most common risk factors for relinquishment to animal shelters and euthanasia for both dogs and cats include house-soiling, destruction, aggression, and hyperactive behavior—all potential clinical signs of anxiety.

Anxiety disorders rarely occur alone, and often occur in combination. Thunderstorm and noise phobias do not necessarily occur simultaneously; however, thunderstorm phobia, noise phobia, and separation anxiety occur significantly more often together than would be expected were these conditions independent. Such evidence suggests that the precise cause of a pet's anxiety could be difficult to isolate, and multiple pathologies could be occurring in the same pet.

Although the "triggers" and manifestation of behavioral disorders in humans may be different, anxiety, fear, and stress contribute to the human disorders. In an effort to alleviate the behavior disorders of human and non-human animals, certain synthetic drugs have been developed.

For instance, clomipramine hydrochloride, fluoxetine hydrochloride, benzodiazepine, and acepromazine maleate are all drug compositions that have been used in an attempt to alleviate anxiety in humans and/or non-human animals. While these drugs may provide some relief from anxiety, a significant downside of these drugs is that they can be sedating, and the human or non-human animal experiences lethargy or sleepiness. Moreover, many of these drugs are synthetic compositions, which humans may be reluctant to ingest or administer to their pets.

The biochemistry of anxiety is extremely complicated and, to a great extent, still poorly understood. Studies have shown that nearly every type of neurotransmitter and hormone, from serotonin, γ-aminobutyric acid (GABA), glutamate, and dopamine to cortisol, adrenaline, and even thyroid hormone can play some role in anxiety. Anxiety, in many ways, is simply the biochemical reaction to brain stress. When something causes any change to the delicate chemical balance in the brain, anxiety is often the result.

The ideal management for anxiety, therefore, should be multi-modal, increasing the likelihood that one or more of the mechanisms of action will target and correct any given underlying chemical imbalance. Common FDA-approved pharmaceuticals such as serotonin-selective re-uptake inhibitors (SSRI's), tricyclic antidepressants (TCA's), and benzodiazepines, however, typically work via a single mechanism of action.

Due to the difficulty in tracking adverse drug reactions in combination drugs, the FDA has become increasingly reluctant to approve drugs with multiple active ingredients. Therefore, a multi-modal approach using pharmaceuticals alone is unlikely. Nutritional and herbal supplements, which are regulated more like foods than drugs by the FDA, represent a novel delivery method for multiple ingredients, offering a much greater opportunity for the multi-modal management of anxiety. For this and other reasons, the use of natural products for human and non-human animals is becoming increasingly popular as consumers seek alternatives to pharmaceuticals. Some of these natural products are being incorporated into dietary supplements and various foods.

In light of the discussion above, the need exists for a natural product composition that has anxiolytic properties. This composition should help support normal behavior and facilitate a calming effect, while not causing extreme lethargy or sleepiness. In turn, such compositions should work synergistically to manage and control the clinical signs or symptoms of anxiety.

SUMMARY

In accordance with the purposes and benefits described herein, in one aspect of the present disclosure an anxiolytic composition is provided comprising a synergistic combination of L-theanine and a whey protein. In embodiments, the whey protein comprises alpha-lactalbumin. The anxiolytic composition provides an anxiolytic change in a release pattern of one or more neurotransmitters including γ-aminobutyric acid (GABA) and serotonin. The composition may be formulated for oral administration to a mammal, including a human, a companion animal, and an equine animal.

In embodiments, the synergistic combination further comprises an extract of *magnolia* and an extract of phellodendron. In embodiments, the synergistic combination further comprises RELORA.

In another aspect, a method is described for reducing, ameliorating, or treating symptoms of anxiety, comprising administration of a synergistic combination of L-theanine and a whey protein to a mammal. In embodiments, the synergistic combination further comprises an extract of *magnolia* and an extract of phellodendron. In embodiments, the whey protein is provided as a whey protein concentrate comprising alpha-lactalbumin. The method further includes orally administering the synergistic combination in an amount sufficient to provide an anxiolytic change in a release pattern of one or more neurotransmitters, including in an embodiment γ-aminobutyric acid (GABA) and serotonin. The mammal may be a human, a canine, a feline, or an equine.

In yet another aspect, an anxiolytic composition is provided comprising a synergistic combination of L-theanine and s-adenosylmethionine (SAMe). The synergistic combination provides an anxiolytic change in a release pattern of one or more neurotransmitters including glutamate and γ-aminobutyric acid (GABA). The composition may be formulated for oral administration to a mammal. In embodiments, the SAMe comprises a SAMe phytate salt.

In still yet another aspect, an anxiolytic composition is provided comprising a synergistic combination of L-theanine, a whey protein, and RELORA. In embodiments, the whey protein comprises alpha-lactalbumin. In embodiments, the whey protein is a whey protein concentrate.

In embodiments, the composition comprises at least 2.0 mg of L-theanine, at least 0.5 mg of whey protein, and at least 0.5 mg of RELORA. In other embodiments, the composition comprises at least 2.0 mg of L-theanine, at least 0.5 mg of whey protein, and at least 3.0 mg of RELORA.

In the following description, there are shown and described several preferred embodiments of the disclosed anxiolytic compositions and associated methods. As it should be realized, the compositions and methods are capable of other, different embodiments and their several details are capable of modification in various, obvious aspects all without departing from the compositions and methods as set forth and described in the following claims. Accordingly, the drawings and descriptions should be regarded as illustrative in nature and not as restrictive.

BRIEF DESCRIPTION OF THE DRAWINGS

The accompanying drawing figures incorporated herein and forming a part of the specification, illustrate several aspects of the disclosed anxiolytic compositions, and together with the description serve to explain certain principles thereof. In the drawings.

Reference will now be made in detail to embodiments of the disclosed anxiolytic compositions, examples of which are illustrated in the accompanying drawing figures.

DETAILED DESCRIPTION

The present invention relates to one or more compositions of *magnolia*, phellodendron, theanine, s-adenosylmethionine (SAMe), and/or whey protein that may be used by any human or non-human animal. In one embodiment, the composition includes *Magnolia officinalis, Phellodendron amurense*, L-theanine, and alpha-lactalbumin. This combination of materials may involve a number of different biochemical processes. Accordingly, the composition provides a multimodal approach to alleviating anxiety. Without intending to be bound by any particular theory, one potential mode is by acting on multiple neurotransmitters (such as glutamate or GABA), increased production of neurotransmitter levels such as serotonin, or by altering brain wave activity.

As further background, *Magnolia officinalis* is a species of *Magnolia* native to China. The bark and/or extract of the *Magnolia officinalis* include honokiol and magnolol, which enhance the activity of both synaptic and extra-synaptic GABA receptors in the brain. GABA is the brain's chief inhibitory neurotransmitter which modulates the activity of overexcited neurons stimulated by fear and anxiety. The action of these compounds is thought to be selective binding to specific GABA receptors which may explain why the effects of honokiol and magnolol are anxiolytic, without causing sedation.

*Phellodendron amurense* is a species of tree commonly called the Amur cork tree. *Phellodendron* fruit, bark and/or extracts are rich in the compound berberine. The combination of *Magnolia* plus *Phellodendron* extracts is synergistic, with the combination controlling stress and anxiety more effectively than either compound used alone. Generally, synergy refers to the effect wherein a combination of two or more components provides a result which is greater than the sum of the effects produced by the agents when used alone. In preferred embodiments of the present invention, the synergistic effect is greater than an additive effect. The synergism observed with *Magnolia* plus *Phellodendron* extracts may be due to the fact that berberine inhibits the release of glutamate by pre-synaptic neurons into the synaptic cleft. The excitatory neurotransmitter glutamate and the inhibitory neurotransmitter GABA are both modulated at the synaptic level by the combination. In a laboratory model, the combination of *Magnolia* and *Phellodendron* reduced anxiety in beagles in a placebo-controlled clinical trial of noise-induced anxiety. In some embodiments of the present invention, the combination of *Magnolia* and *Phellodendron* may be administered as a commercially available preparation (RELORA; InterHealth Nutraceuticals, Inc., Benicia, Calif.).

The neurotransmitters glutamate and GABA work antagonistically to regulate interactions among neurons in the brain. Glutamate is the primary excitatory neurotransmitter, making neurons more susceptible to stimuli and electrical stimulation. Glutamate plays a significant role in fear and anxiety, which are often the result from over-stimulated neurons. GABA is the primary inhibitory neurotransmitter in the nervous system and plays an equally essential role in controlling anxiety by dampening and/or reversing the effects of glutamate.

In one embodiment, the combination of *Magnolia* plus *Phellodendron* extracts is synergistic, with the combination controlling stress and anxiety more effectively than either compound used alone. This synergism is due to the effects these compounds have on both glutamate and GABA at the synaptic level. *Magnolia officinalis* extracts, more specifically the constituents honokiol and magnolol, enhance the activity of both synaptic and extra-synaptic GABA receptors in the brain. *Phellodendron amurense* extracts contain berberine. Berberine inhibits the release of glutamate by pre-synaptic neurons into the synaptic cleft. *Magnolia* extracts, therefore, enhance the effects of stabilizing GABA while berberine from *Phellodendron* extracts blocks the release of excitatory glutamate.

Berberine is a bright yellow ammonium salt found in *Phellodendron amurense*, and can also be found in such plants as the Oregon grape, barberry, goldenseal, goldenthread, and tree turmeric. Berberine is usually found in the roots, rhizomes, stems, and bark.

L-theanine is a structural analogue of the amino acid glutamate, the most important excitatory neurotransmitter of the nervous system. Theanine, found naturally in many types of tea, is thought to exert neuro-protective effects by binding and blocking glutamate receptors, thus reducing excitatory impulses and lowering the stimulatory effects of glutamate. Theanine increases the levels of stabilizing neurotransmitters such as serotonin, dopamine, and GABA in the brain. Theanine also directly stimulates the production of alpha brain waves, which create a state of deep relaxation, wakefulness, and mental alertness.

Alpha-lactalbumin is a component of certain whey protein compositions and a high-quality protein source which supplements amino acids in animals. Milk has long been considered a beverage with post-prandial calming properties, especially in infants and young animals. The first human studies on the anxiolytic effects of milk originated in the 1930's and confirmed the calming effects of certain proteins in milk. Alpha-lactalbumin exerts neuro-protective properties by providing amino acid precursors to the antioxidant glutathione (cysteine) and the mood-enhancing neurotransmitter serotonin (tryptophan).

Since the brain consumes approximately 20% of the oxygen utilized by the body, reactive oxygen species (ROS) are generated at extremely high rates, and brain cells are especially prone to oxidative damage. A loss of neurons in the mature brain cannot be compensated with the generation of new neurons, therefore the imbalance between the production of ROS and antioxidants has been implicated in several neurological disorders. Glutathione is the predominant antioxidant in the nervous system. The glutathione content of brain cells depends strongly on the availability of precursors of glutathione. Alpha-lactalbumin supplements cysteine, the amino acid precursor to glutathione.

Brain serotonin levels increase under stress since the neurotransmitter is important in regulating emotional states and moods. Chronic stress and anxiety may lead to a depletion of available concentrations of serotonin and its precursor tryptophan, causing serotonin to fall below functional needs. Alpha-lactalbumin contains tryptophan and a mix of other amino acids from a natural food protein source, and studies suggest that dietary supplementation of alpha-lactalbumin improves cognitive performance in stress-vulnerable subjects via increased brain tryptophan and serotonin activities. In one embodiment, alpha-lactalbumin synergizes the serotonergic effects of the other ingredients in the formulation, thus providing an additional mode of action.

S-adenosylmethionine (SAMe) is a naturally occurring compound that is present in tissues throughout the body. At the molecular level, SAMe is involved in various metabolic pathways, including transmethylation, trans sulfuration, and aminopropylation. In the body, SAMe is synthesized from an amino acid, methionine, and a triphosphate nucleotide, ATP. SAMe is in turn involved in the biosynthesis of numerous biological molecules, including hormones and neurotransmitters.

Administering SAMe to subjects has been found to have a variety of salutary effects. SAMe regulates gene expression and helps prevent genetic mutations; it maintains mitochondrial function; it participates in phospholipid synthesis and maintains the integrity of cell membranes; and it regulates neurotransmitters such as serotonin, dopamine and epinephrine (adrenaline), and hormones such as estrogen and melatonin. SAMe is also known to inhibit neuron death following ischemia; improve the utilization of glucose in the brain; inhibit brain edema; improves EEG and evoked potential findings by normalizing them; and improve motor function, such as that impaired by stroke. SAMe has been found, for example in meta-analyses of multiple drug studies, to enhance emotional well-being and is as effective as many common prescription drugs in treating depression, but with significantly fewer side effects than any of these drugs. SAMe has also been used to treat anxiety, chronic pain, arthritis, rheumatoid fibromyalgia, Chronic Fatigue Syndrome, cognitive difficulties associated with Alzheimer's Disease, neurovascular disease and neurological conditions associated with AIDS. In addition to diseases of the central and peripheral nervous system, SAMe has been found to improve diseases of the joints, cardiovascular system, and liver.

SAMe administration was initially considered impractical, due to the instability of the SAMe ion during manufacturing, shipping, and storage. Eventually stable salts of SAMe were developed (such as SAMe tosylate disulfate, the butanedisulfonate salt of SAMe, the di-para-toluene sulfonate disulfate salt of SAMe, the tri-para-toluene sulfonic acid salt of SAMe, butanedisulphonate salt of SAMe, and disulfate p-toluensulfonate salt of SAMe). In some exemplary embodiments of the present invention, SAMe is administered as a commercial SAMe salt of phytic acid.

The skilled artisan will appreciate that the composition of *Magnolia officinalis, Phellodendron amurense*, L-theanine, and whey protein may include any amount of each ingredient. The ingredients may also be concentrates, such as a whey protein concentrate. Moreover, the composition can be used by a human or non-human animal (e.g. mammal, avian, fish, reptilian, etc.) subjects.

In one embodiment, the composition for non-human animals may contain between 0.5-3 mg *Magnolia officinalis,* 0.03-0.2 mg *Phellodendron amurense,* 17.0-450 mg L-theanine, and 12.0-100 mg alpha-lactalbumin. However, in another embodiment, the composition for non-human animals may contain between 0.01 mg-10 g *Magnolia officinalis,* 0.01 mg-10 g *Phellodendron amurense,* 0.01 mg-10 g L-theanine, and 0.01 mg-10 g alpha-lactalbumin.

In one embodiment, the composition may contain at least 0.5 mg of RELORA, at least 2.0 mg of L-theanine, at least 0.5 mg of whey protein, and at least 1.5 mg of SAMe.

In one embodiment, the composition for non-human animals such as canines may contain at least 6.0 mg of RELORA, at least 3.0 mg of L-theanine, at least 1.0 mg of whey protein, and at least 3.0 mg of SAMe.

In one embodiment, the composition for non-human animals such as felines may contain at least 3.0 mg of RELORA, at least 2.0 mg of L-theanine, at least 0.5 mg of whey protein, and at least 1.0 mg of SAMe.

In one embodiment, the composition for non-human animals such as equine animals may contain at least 20.0 mg of RELORA, at least 15.0 mg of L-theanine, at least 5.0 mg of whey protein, and at least 10.0 mg of SAMe.

In one embodiment, the composition for humans may contain at least 20.0 mg of RELORA, at least 15.0 mg of L-theanine, at least 5.0 mg of whey protein, and at least 10.0 mg of SAMe.

In one embodiment for companion animals such as canines or felines, the composition comprises 37 mg of RELORA, 17 mg L-theanine and 12 mg of whey protein in a single dosage form.

In one embodiment for companion animals such as canines or felines, the composition comprises 75 mg of RELORA, 35 mg L-theanine and 25 mg of whey protein in a single dosage form.

In one embodiment for companion animals such as canines or felines, the composition comprises 450 mg of RELORA, 205 mg L-theanine and 100 mg of whey protein in a single dosage form.

In one embodiment for companion animals such as canines or felines, the composition comprises 0.5 mg *Magnolia officinalis* extract, 0.03 mg *Phellodendron amurense* extract, 17 mg L-theanine and 12 mg alpha-lactalbumin in a single dosage form.

In one embodiment for equine animals, the composition comprises 750 mg of RELORA, 150 mg of L-theanine, 1000 mg of whey protein.

In one embodiment for equine animals, the composition comprises 1500 mg of RELORA, 300 mg of L-theanine, 1000 mg of whey protein.

One will appreciate that any combination of *magnolia*, phellodendron, theanine, and/or whey protein (or alpha-lactalbumin) may be combined. For instance, in one embodiment, the composition comprises *magnolia* extract and alpha-lactalbumin, without phellodendron or theanine. Alternatively, the composition may include phellodendron extract and alpha-lactalbumin without *magnolia* or theanine. Again, any single component of *magnolia*, phellodendron, theanine, and/or whey protein (or alpha-lactalbumin) that provides the desired response or any combination of multiple components can be provided. The formulation may also include various other flavonoids, omega-3 fatty acids, eicosapentaenoic acid (EPA) and docosahexaenoic acid (DHA), valerian, SAMe, other milk proteins, or other milk proteins (such as alpha-S1 Tryptic casein) or products containing milk proteins, and/or *Sceletium tortuosum*.

The composition can be combined in any manner and presented to the human or non-human animal in any combined form. In one embodiment, the composition comprises a unit dosage form, including but not limited to pharmaceutical dosage forms suitable for oral, rectal, intravenous, subcutaneous, intramuscular, transdermal, transmucosal, and topical.

In one embodiment, the composition comprises an orally administrable dosage form. Examples of orally administrable dosage forms include, but are not limited to a tablet, capsule, powder that can be dispersed in a liquid or sprinkled on food, a liquid such as a solution, suspension, or emulsion, a soft gel/chew capsule, a chewable bar, or other convenient dosage form known in the art. In some embodiments, the composition comprises a tablet, capsule, or soft chewable treat. The orally administrable dosage forms may be formulated for immediate release, extended release or delayed release. The composition may be coated or uncoated.

Example 1. Evaluation of Neurotransmitter Release Patterns in Hippocampal Dialysate Samples of C57Bl/6 Mice after 7 Day Treatment with an Anxiolytic Composition Neurotransmitter release patterns in the brain were measured by a procedure which involved inserting a probe into the hypothalamus region (microdialysis probe) of a laboratory animal and flushing the probe via dialysis with an artificial cerebrospinal fluid (CSF). This is an accepted and common method used to obtain and measure in vivo brain levels of neurotransmitters and other small proteins.

The fluid being collected represents the extracellular or interstitial fluid found in the hippocampal region of the brain. This area is usually the preferred and typical area for microdialysis analysis because any changes measured in this area of the brain are believed to correspond with approximately 80% of whole brain tissue. The levels of neurotransmitters in the fluid represent a complex balance between the release of these neurotransmitters by pre-synaptic neurons, the re-uptake of these neurotransmitters back into the neurons, as well as any interactions between neurotransmitters. Therefore, the results indicate how compounds and their combinations affect brain neurochemistry.

For the evaluation, male C57BI mice were divided into groups (6 per group) and administered a variety of compounds or a placebo orally for seven days. On day 6, each mouse was anesthetized and a microdialysis probe was inserted into the hippocampus region of the brain. Microdialysis sampling began the day after surgery, with each probe being connected to a microperfusion pump and perfused with an artificial CSF. Samples were taken in 30 minute aliquots beginning 90 minutes prior to dosing of each compound on the 7th day. Each aliquot was then analyzed to determine the amount of GABA, glutamate, and serotonin (5-HT) in each sample. Analysis of the neurotransmitters was performed in two stages in an attempt to identify the chronic and acute effects of each compound.

In the described results, Compound A is L-theanine; Compound B is a composition comprising an extract of *Magnolia officinalis* and an extract of *Phellodendron amurense*; Compound C is a milk whey protein comprising alpha-lactalbumin, Compound D is SAMe; and Compound E is glutathione. In embodiments, Compound B was provided as a commercially available preparation (RELORA; InterHealth Nutraceuticals, Inc., Benicia, Calif.). In embodiments, Compound C was standardized to 80% alpha-lactalbumin. In embodiments, Compound D was provided as a commercially available SAMe phytate salt. Compound A was administered at a dose of 6.66 mg/kg. Compound B was administered at a dose of 12.5 mg/kg. Compound C was administered at a dose of 2.36 mg/kg. Compound D was administered at a dose of 6.02 mg/kg. Compound E was administered at a dose of 13.6 mg/kg. Equivalent dosages for cross-species extrapolation can be calculated by one skilled in the art using conventional dose conversion methods.

Basal Neurotransmitter Output.

First, basal output levels of each neurotransmitter were measured to determine any long-term, chronic effects of each compound on the neurotransmitters. Basal levels represent the lowest levels of each neurotransmitter in a 24 hour cycle. These levels were determined by averaging the levels of each neurotransmitter in the three, 30-minute aliquots prior to the administration of the 7th daily dose (Sample −90 min to −60, Sample −60 minutes to −30, and Sample −30 minutes to time 0). The basal levels were measured as a representation of the chronic effects of the compounds on the levels of the neurotransmitters, i.e. measuring what should be lowest effect observed prior to a new dose. To determine the acute effects of these compounds, the levels of each neurotransmitter were then analyzed in the aliquots following dosing for up to 3½ hours (210 minutes) following the 7th daily administration of each compound/combination.

The basal output of serotonin (5-HT), GABA, and glutamate was measured following 6 days of administration of each of the individual components of the described composition as well as the combination of ingredients. The mean concentration of each neurotransmitter was then compared to the mean basal output measured in the placebo group using a student's t-test to determine if the two sets of data are significantly different.

Figure 1:
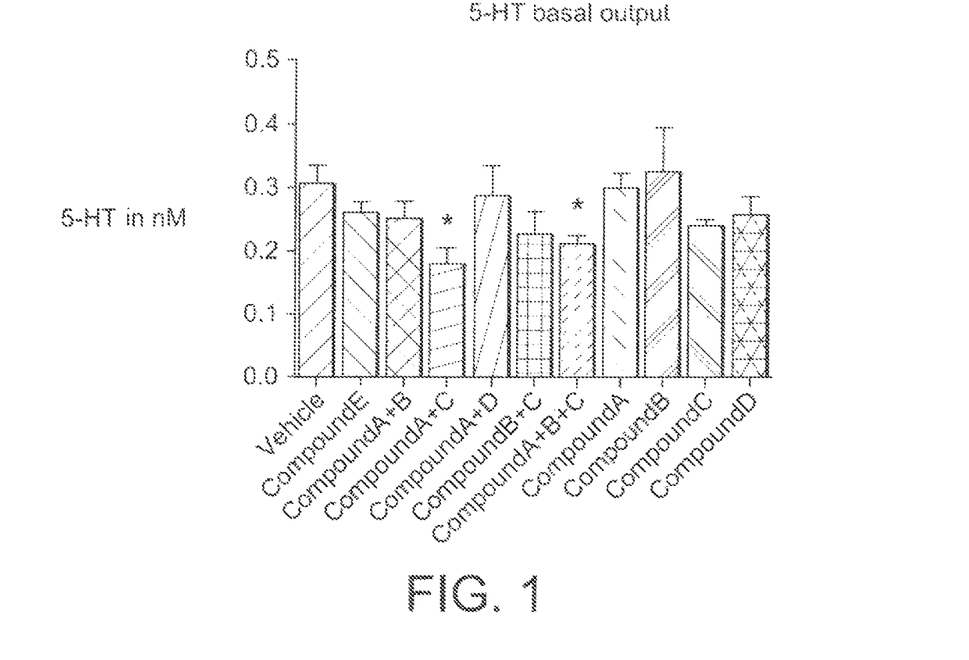
FIG. 1 illustrates basal serotonin (5-HT) output following administration of compositions according to the present disclosure.

With respect to serotonin, individually no single one of the evaluated compounds had a statistically significant effect (p-value<0.05) on the basal output of serotonin (See FIG. 1). That is, for example, individually none of L-theanine, Relora, nor milk whey protein had any significant effect on the basal serotonin levels. On the other hand, the combination of Compounds A+B+C (theanine+*magnolia*/phellodendron+milk whey protein), however, did have a statistically significant effect on basal serotonin levels (p<0.05). The combination of L-theanine and milk whey protein (A+C) also significantly lowered basal serotonin levels. These results demonstrate an unexpected synergistic effect on brain serotonin levels of the combination.

Figure 2:
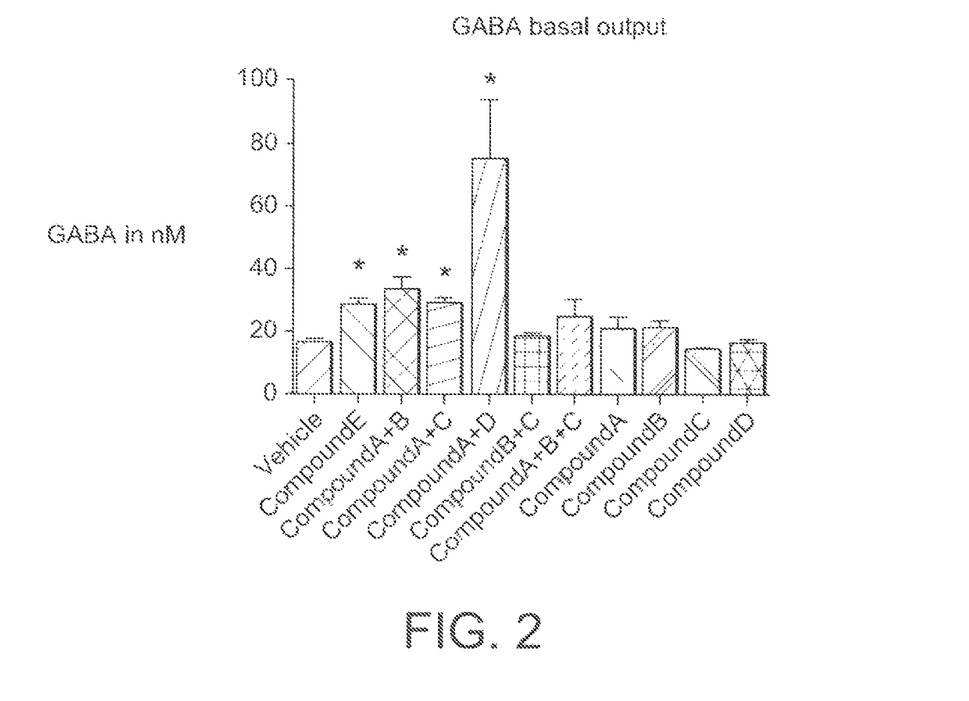
FIG. 2 illustrates basal GABA output following administration of compositions according to the present disclosure.

The combinations of theanine/*magnolia*/phellodendron (A+B) and L-theanine and milk whey protein (A+C) produced an unexpected and synergistic increase in GABA levels (see FIG. 2) Likewise, the combination of theanine and SAMe (A+D) significantly increased basal GABA output.

Figure 3:
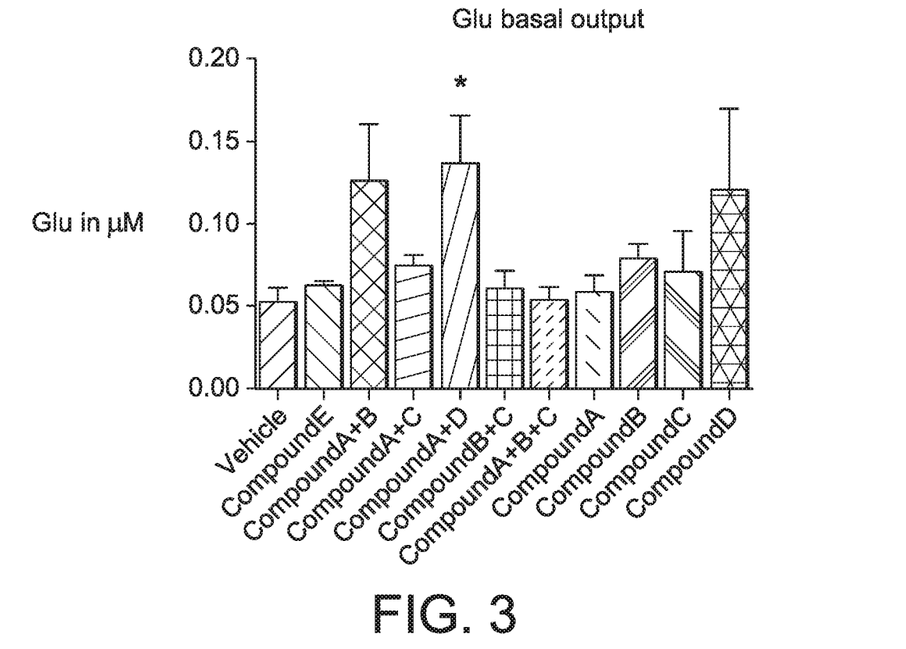
FIG. 3 illustrates basal glutamate output following administration of compositions according to the present disclosure.

For basal glutamate output (see FIG. 3), the combination of theanine/*magnolia*/phellodendron (A+B) showed an increase. Likewise, the combination of theanine and SAMe (A+D) significantly increased basal glutamate output.

Acute Neurotransmitter Output

Following administration of the $7^{th}$ dose of each compound and/or combination, aliquots of CSF were collected in 30-minute increments up to 210 minutes following dosing. The concentration of neurotransmitters in each aliquot represents acute, shorter-term changes in the levels which may not be represented in the basal output results.

The results are plotted in graphs wherein the x-axis represents the time after administration of the $7^{th}$ daily dose, while the y-axis represents a % increase/decrease of the basal output found in the prior portion of the study. This measurement is used because the actual concentrations of neurotransmitters can vary significantly between subject to subject. This method allows for a standardization of the data, and, in essence, allows for each animal to serve as its own individual control. The results were then analyzed using an analysis of variance (ANOVA) to detect any statistically significant treatment effects.

Figure 4:
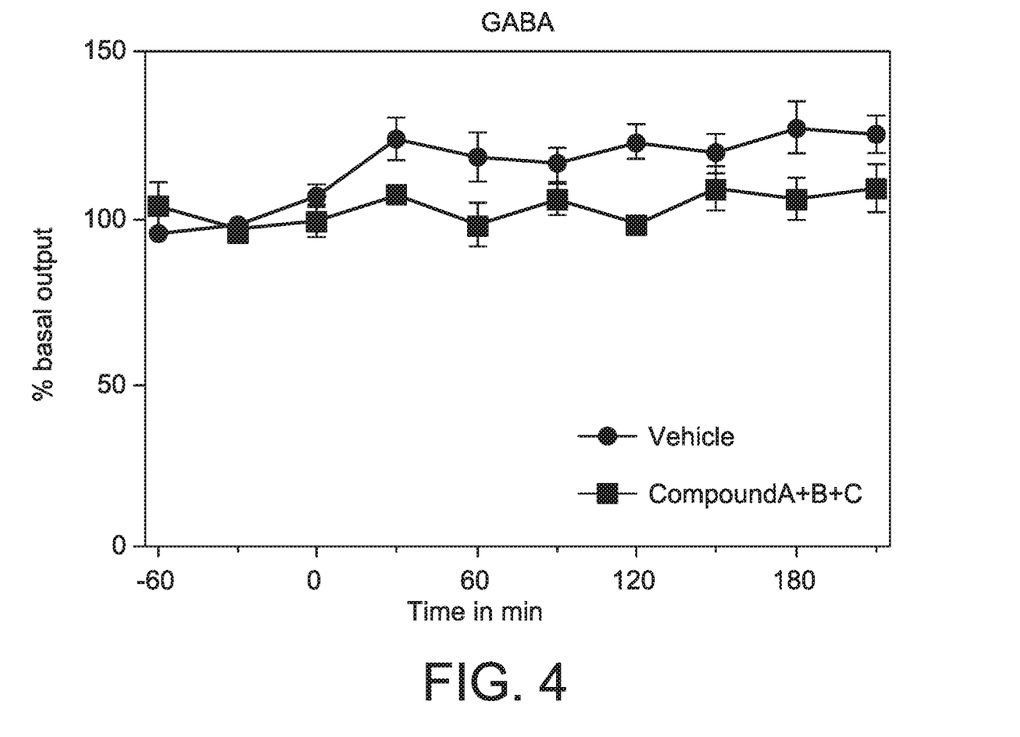
FIG. 4 illustrates a pairwise comparison of GABA output following administration of an embodiment of a composition according to the present disclosure.

Looking at the acute effects of these compounds on GABA first, no statistically significant treatment effects were seen via ANOVA (p<0.05) for the individual compounds A, B, or C when compared to the placebo during the test period. There was, however, a significant treatment effect of the combination of ingredients (A+B+C) when compared to placebo when analyzed by ANOVA, as seen in FIG. 4. Therefore, these results indicate that there is a significant synergistic effect on GABA with the combination of L-theanine and *magnolia*/phellodendron and milk whey protein (A+B+C), whereas each individual component by itself has no effect.

Figure 5:
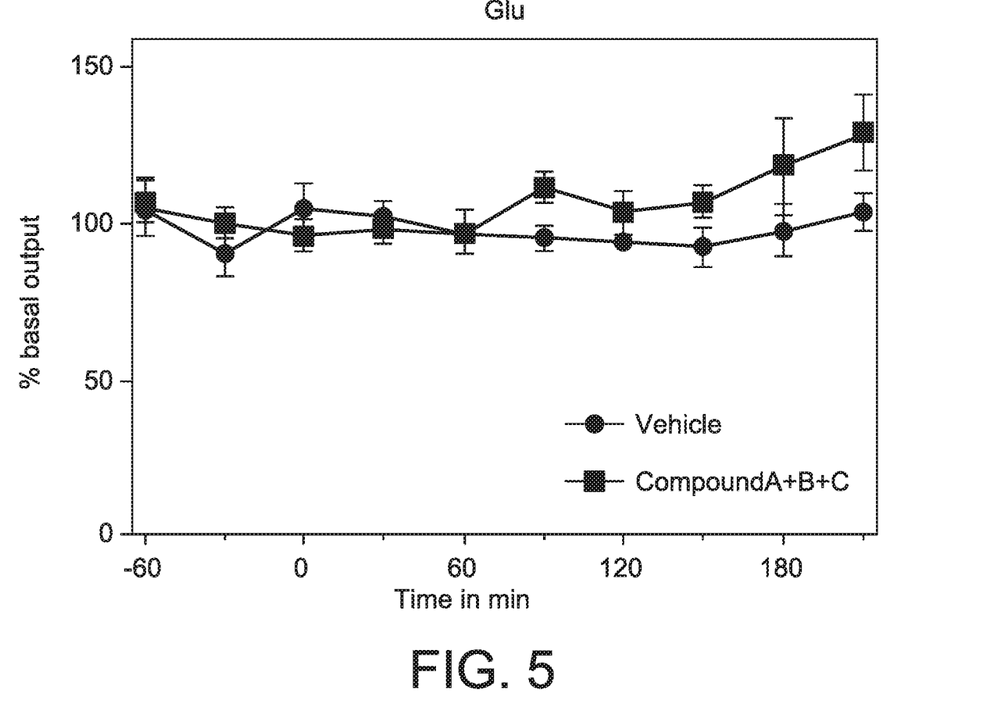
FIG. 5 illustrates a pairwise comparison of glutamate output following administration of the embodiment of FIG. 4.

With respect to glutamate, neither the individual components (A, B, C) nor the combination (A+B+C) had an immediate treatment effect on glutamate levels. However, the results demonstrated a trend indicating a treatment effect by the combination (A+B+C) 120 to 210 minutes following administration (see FIG. 5). The skilled artisan will appreciate that changes in glutamate levels are one of the more difficult neurotransmitter changes to elicit.

Example 2. Evaluation of Anxiolytic Properties of the Disclosed Compositions by Behavioral Testing Wistar rats (16 per group) were dosed either with individual components (L-theanine, *magnolia*/phellodendron, and milk whey protein) or several combinations of the three, including the three-way combination (theanine+*magnolia*/phellodendron+milk whey protein). *Magnolia*/phellodendron combination was provided as a commercially available preparation (RELORA; InterHealth Nutraceuticals, Inc., Benicia, Calif.). Administered milk whey protein was standardized to 80% alpha-lactalbumin. The rats were dosed daily for 14 days, and then a series of behavioral assays were performed to detect any anxiolytic effects on the rats or sedative effects. The treatment groups were as follows:
1: L-theanine+*magnolia*/phellodendron
2: L-theanine+Milk Whey Protein
3: *magnolia*/phellodendron+Milk Whey Protein
4: L-theanine+*magnolia*/phellodendron+Milk Whey Protein
5: L-theanine
6: *magnolia*/phellodendron
7: Milk Whey Protein Animals were placed in the following groups:

| Group Number | Treatment | Daily Dose | Dose Concentration | Dose Volume | Dosing Route | Total # of Animals |
|---|---|---|---|---|---|---|
| 1 | #1 | 50 mg/kg | 10 mg/ml | 5 ml/kg | PO | 16 ♂ |
| 2 | #2 | 24 mg/kg | 4.8 mg/ml | 5 ml/kg | PO | 16 ♂ |
| 3 | #3 | 42 mg/kg | 8.4 mg/ml | 5 ml/kg | PO | 16 ♂ |
| 4 | #4 | 58 mg/kg | 11.6 mg/ml | 5 ml/kg | PO | 16 ♂ |
| 5 | #5 | 16 mg/kg | 3.2 mg/ml | 5 ml/kg | PO | 16 ♂ |
| 6 | #6 | 34 mg/kg | 6.8 mg/ml | 5 ml/kg | PO | 16 ♂ |
| 7 | #7 | 8 mg/kg | 1.6 mg/ml | 5 ml/kg | PO | 16 ♂ |
| 8 | Vehicle (Sterile Water) | 0 mg/kg | 0 mg/ml | 5 ml/kg | PO | 16 ♂ |

Elevated Plus-Maze Test

The elevated plus-maze (EPM) capitalizes on the natural aversion (trait anxiety) of rodents on brightly lit, open, and elevated areas. The EPM has very strong predictive ability and is often used to profile the potential anxiolytic activity of compounds. During this test, the rats are videotaped after being placed in the elevated maze. The videos are analyzed to determine the % of time the rats stay in the open, elevated portions of the maze. Rats that spend more time in the open arms are presumed to be less anxious. Table 1 below represents the average amount of time each rat spent in the open arms of the maze.

TABLE 1

| Treatment | Mean % Time in open arms ± SEM |
|---|---|
| Vehicle | 10 ± 2 |
| 1 | 19 ± 3 |
| 2 | 15 ± 2 |
| 3 | 18 ± 3 |
| 4 | 13 ± 3 |
| 5 | 13 ± 2 |
| 6 | 12 ± 3 |
| 7 | 11 ± 2 |

Figure 6A:
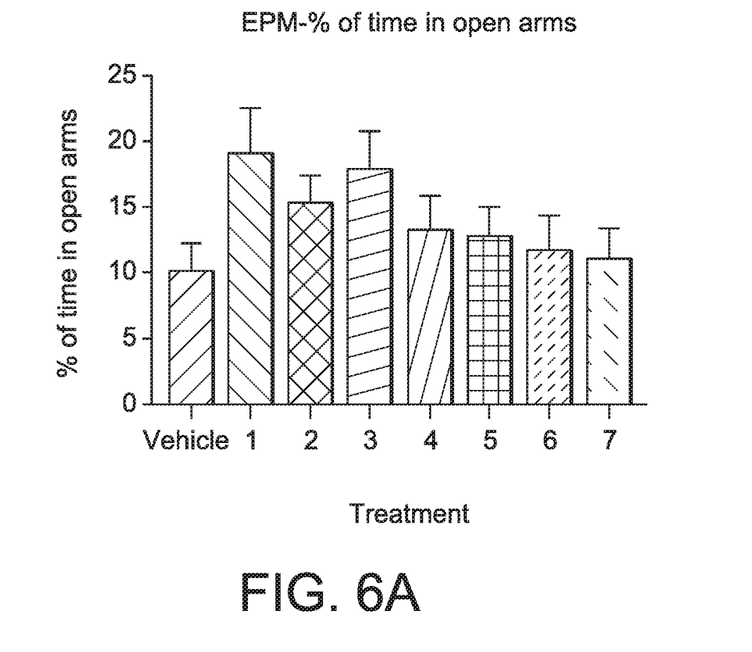
FIG. 6A illustrates results of an Elevated-Plus Maze (EPM) test following administration of compositions according to the present disclosure.
Figure 6B:
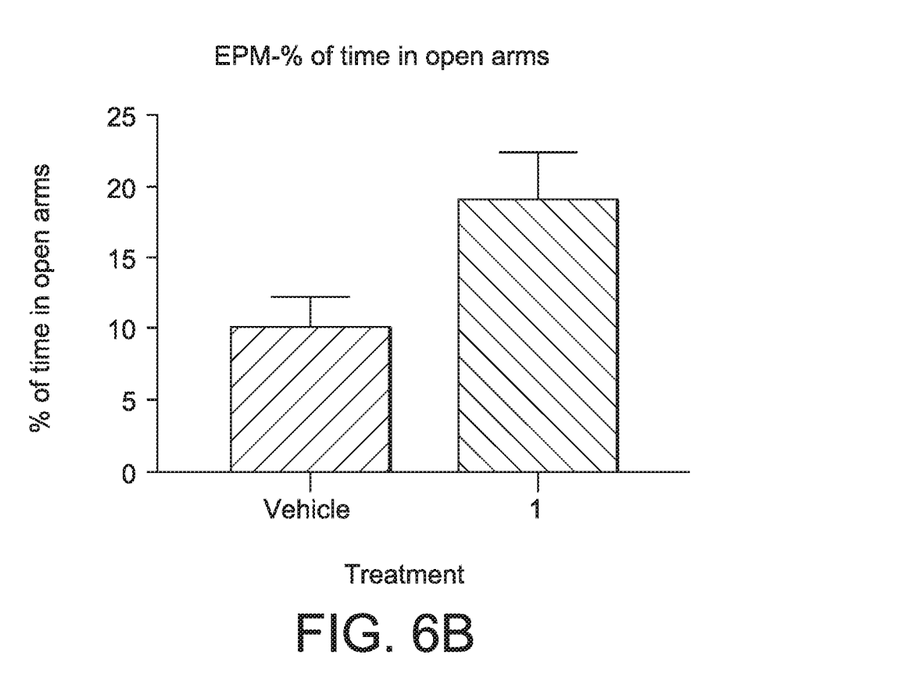
FIG. 6B illustrates a pairwise comparison of the EPM test following administration of an embodiment of a composition according to the present disclosure.
Figure 6C:
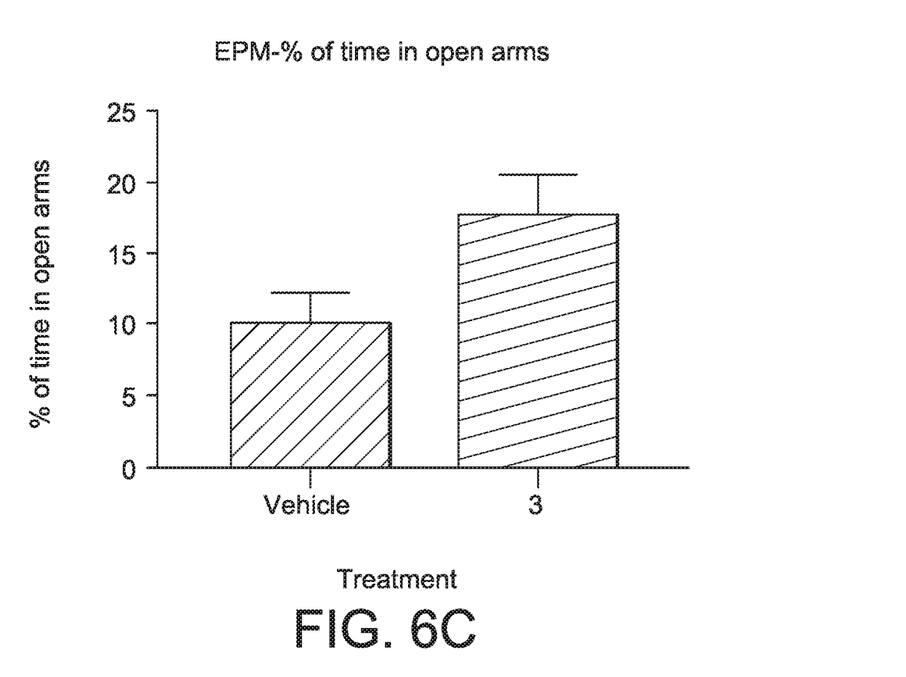
FIG. 6C illustrates a pairwise comparison of the EMP test following administration of another embodiment of a composition according to the present disclosure.

In this study, the rats administered the combination of ingredients in Treatment 4 spent, on average, 3 minutes longer in the open arms of the maze than the rats administered a placebo (see FIG. 6A), indicating an anxiolytic effect of the compounds. Similarly, the combination of L-theanine/milk whey protein (treatment 2) spent, on average, 5 minutes longer in the open arms of the maze than the rats administered a placebo (see FIG. 6), indicating an anxiolytic effect of the compounds. The combinations of L-theanine/*magnolia*/phellodendron (treatment 1) and *magnolia*/phellodendron/milk whey protein (treatment 3) showed a statistically significant effect in post hoc pairwise comparisons (both at $p<0.05$; see FIGS. 6B and 6C, respectively).

Open-Field Activity as a Measure of Sedation

Locomotor activity in an open field test is a good measure of the sedative properties of a compound. As one example, a noted side-effect of many anxiolytic compounds such as benzodiazepines is marked sedation in conjunction with administration. These products are quite effective anxiolytics, but patients are often saddled with the undesirable effects of sedation.

This test is performed by placing a rat in an open, brightly lit enclosure. The rats are videotaped, and the total distance the rat travels during the testing period is recorded as an indicator of locomotor activity. Sedated rats will travel less, while active rats will travel farther total distances.

TABLE 2

| Treatment | Mean Distance (cm) ± SEM |
|---|---|
| Vehicle | 9062 ± 597 |
| 1 | 11735 ± 447 |
| 2[a] | 10887 ± 1055 |
| 3 | 11068 ± 814 |
| 4 | 9833 ± 789 |
| 5 | 9971 ± 652 |
| 6 | 10224 ± 635 |
| 7 | 10191 ± 643 |

[a]One rat removed from analysis due to inaccurate video tracking

Figure 7A:
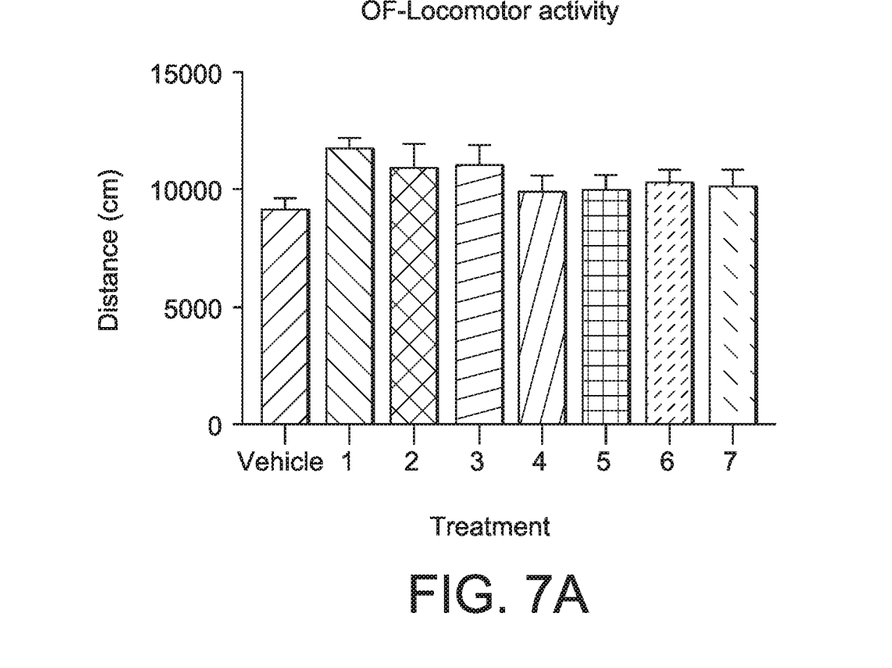
FIG. 7A illustrates results of an Open Field (OF) test following administration of compositions according to the present disclosure.
Figure 7B:
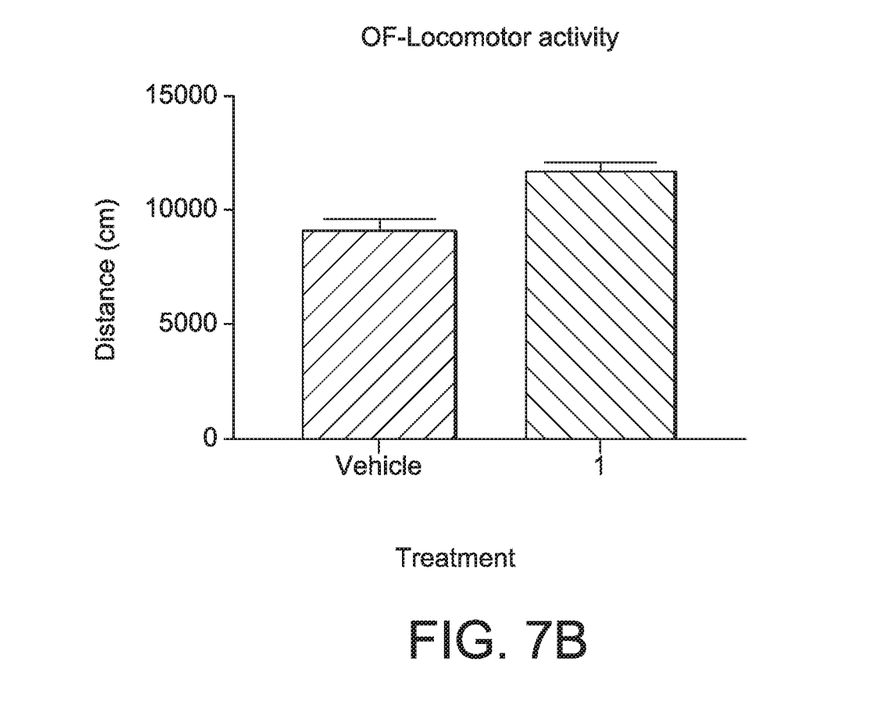
FIG. 7B illustrates a pairwise comparison of the OF test following administration of an embodiment of a composition according to the present disclosure.
Figure 7C:
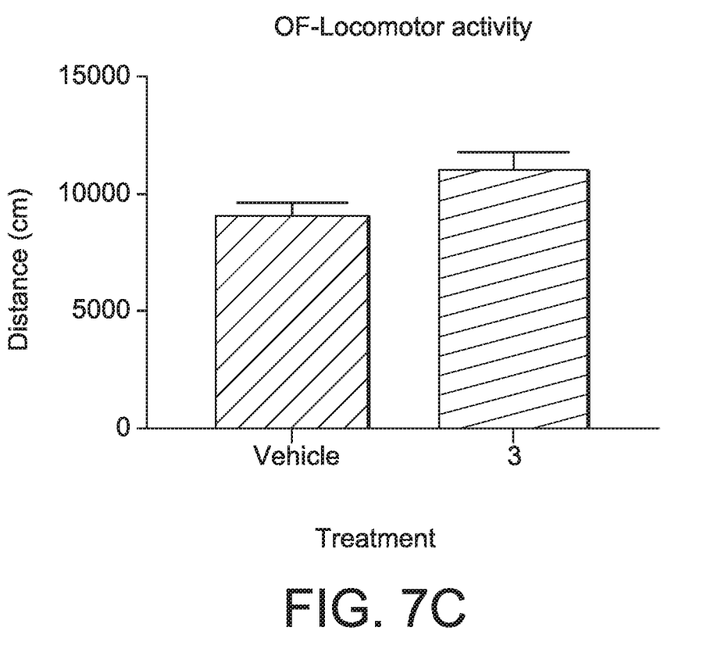
FIG. 7C illustrates a pairwise comparison of the OF test following administration of another embodiment of a composition according to the present disclosure.

The results presented in Table 2 and FIG. 7A indicate that none of the compounds/combinations administered appear to have a sedative effect on the locomotor activity of the rats. All rats were more active than the placebo, indicating an enhanced desire to explore and investigate, and indeed post hoc pairwise comparisons indicated a trend towards increased locomotor activity, particularly for Treatment 1 [O30]=3.58, $p<0.01$; t-test] and Treatment 3 [O30]=1.99, $p=0.06$; t-test] (see FIGS. 7B and 7C). Compounds which have an anxiolytic effect without sedation are thought to be extremely desirable candidates for treatment of anxiety.

Accordingly, by the foregoing results it will be appreciated that an effective composition suitable for oral administration is provided which in various embodiments affects brain neurochemistry as shown by alterations in release patterns of various neurotransmitters. In turn, various behavioral evaluations demonstrated an anxiolytic effect of various embodiments of the described compositions. While individual compounds of the described compositions had no effect on brain neurochemistry or behavior, surprisingly a synergistic effect of the compositions was seen. The foregoing has been presented for purposes of illustration and description. It is not intended to be exhaustive or to limit the embodiments to the precise form disclosed. Obvious modifications and variations are possible in light of the above teachings. The embodiments described above were chosen to provide the best application to thereby enable one of ordinary skill in the art to utilize the disclosed inventions in various embodiments and with various modifications as are suited to the particular use contemplated. All such modifications and variations are within the scope of the appended claims when interpreted in accordance with the breadth to which they are fairly, legally and equitably entitled.

What is claimed:

1. An anxiolytic composition comprising a synergistic combination of L-theanine and a whey protein provided at a ratio of about 3:1, wherein the synergistic combination provides an anxiolytic change in a release pattern of one or more neurotransmitters.

2. The anxiolytic composition of claim 1, wherein the whey protein comprises alpha-lactalbumin.

3. The anxiolytic composition of claim 1, wherein the neurotransmitters are brain neurotransmitters selected from the group consisting of γ-aminobutyric acid (GABA) and serotonin.

4. The anxiolytic composition of claim 1, formulated for oral administration to a mammal.

5. The anxiolytic composition of claim 4, wherein the mammal is selected from the group consisting of a human, a companion animal, and an equine animal.

6. A method for reducing, ameliorating, or treating symptoms of anxiety, comprising administration of a combination of L-theanine and a whey protein at a ratio of about 3:1 to a mammal whereby an anxiolytic change in a release pattern of one or more neurotransmitters is effected.

7. The method of claim 6, further including providing the whey protein as a whey protein concentrate comprising alpha-lactalbumin.

8. The method of claim 6, wherein the neurotransmitters are brain neurotransmitters selected from the group consisting of γ-aminobutyric acid (GABA) and serotonin.

9. The method of claim 6, wherein the mammal is a canine or feline.

10. The method of claim 6, wherein the mammal is an equine.

* * * * *